United States Patent [19]
Sinnott et al.

[11] Patent Number: 5,447,960
[45] Date of Patent: Sep. 5, 1995

[54] FUNGICIDAL USE OF PHENOLIC AROMATIC COMPOUNDS

[75] Inventors: Deirdre M. Sinnott, Childrey Near Wantage, England; Hak-Fun Chow, Wanchai, Hong Kong; Robert J. Ehr, Brownsburg, Ind.; Steven D. Lubetkin, Wantage, England; Stephen E. Bales; Muthiah N. Inbasekaran, both of Midland, Mich.

[73] Assignee: DowElanco, Indianapolis, Ind.

[21] Appl. No.: 131,517

[22] Filed: Oct. 4, 1993

[51] Int. Cl.6 .................. A01N 31/08; A01N 43/14; A01N 43/16; A01N 43/42

[52] U.S. Cl. .................. 514/732; 514/297; 514/437; 514/454

[58] Field of Search ........................ 514/732

[56] References Cited

U.S. PATENT DOCUMENTS

| | | | |
|---|---|---|---|
| 4,467,122 | 8/1984 | Szabolce | 568/727 |
| 4,684,678 | 8/1987 | Schultz et al. | 523/466 |
| 4,707,534 | 11/1987 | Schultz | 528/97 |
| 4,965,395 | 10/1990 | Saeki et al. | 560/11 |

FOREIGN PATENT DOCUMENTS 2201673B 1/1991 United Kingdom.

OTHER PUBLICATIONS

Chemical Abstracts, vol. 76, No. 19, p. 16 (May 8, 1972), abstracting Kuyantseva, *Antimycotic properties of ten acridan derivatives*, Aktual. Vop. Farm, 1970, pp. 202–204, Russia.

Primary Examiner—Allen J. Robinson
Attorney, Agent, or Firm—Donald R. Stuart

[57] ABSTRACT

A plant fungicide method comprises applying to the locus of a plant pathogen a fungicidally effective amount of a compound of formula (I)

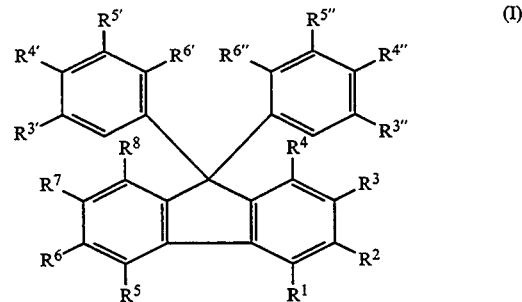

or a salt or a complex thereof, wherein:
$R^1$, $R^2$, $R^3$, $R^4$, $R^5$, $R^6$, $R^7$, and $R^8$ are independently H, halo, $NO_2$, ($C_1$-$C_4$) alkyl, or halo($C_1$-$C_4$) alkyl;
$R^{3'}$, $R^{4'}$, $R^{5'}$, $R^{3''}$, $R^{4''}$, and $R^{5''}$ are independently H, halo, OH, or $CH_3$, provided that at least one is OH;
$R^{6'}$ and $R^{6''}$ are independently H or OH.

9 Claims, No Drawings

FUNGICIDAL USE OF PHENOLIC AROMATIC COMPOUNDS

This invention provides a new method of combating plant pathogens. More specifically, the invention provides a new method of combating plant pathogens utilizing phenolic aromatic compounds of formula (I):

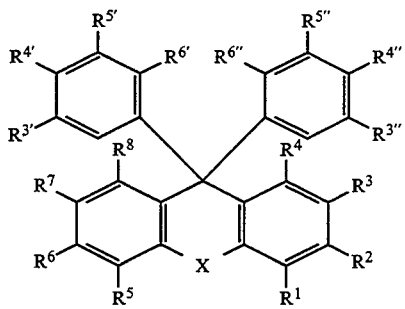

wherein:
$R^1$, $R^2$, $R^3$, $R^4$, $R^5$, $R^6$, $R^7$, and $R^8$ are independently H, halo, COOH, $NH_2$, $NO_2$, CN, ($C_1$–$C_4$) alkyl, halo ($C_1$–$C_4$) alkyl, ($C_1$–$C_4$) alkoxy, $COR^9$, $COOR^9$, or $CONR^9$;

$R^9$ is ($C_1$–$C_4$) alkyl;

X is O, S, SO $SO_2$ $CR^{10}R^{11}$, C=$CH_2$, CO, NO or $NR^{10}$, or X is a single bond connecting the two adjacent carbon atoms;

$R^{10}$ and $R^{11}$ are independently H, OH, ($C_1$–$C_4$) alkyl, ($C_2$–$C_4$) alkenyl, ($C_1$–$C_4$) alkoxy, substituted ($C_1$–$C_4$) alkyl, substituted ($C_2$–$C_4$) alkenyl, substituted ($C_1$–$C_4$) alkoxy, benzyl, or substituted benzyl;

$R^{3'}$, $R^{4'}$, $R^{5'}$, $R^{3''}$, $R^{4''}$, and $R^{5''}$ are independently H, halo, OH, $CH_3$, $OCH_3$,

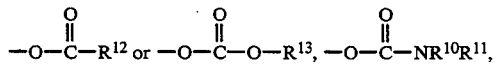

or O—$SO_2$—$R^{12}$ provided that at least one is OH;

$R^{6'}$ and $R^{6''}$ are independently H or OH or $R^{6'}$ and $R^{6''}$ combine to form —O—;

$R^{12}$ is H, ($C_1$–$C_{16}$) alkyl, or ($C_1$–$C_{16}$) alkyl substituted with $COOR^{14}$, phenyl, or phenyl substituted with halo, hydroxy, amino, nitro, ($C_1$–$C_4$) alkoxy, or COOH;

$R^{13}$ is ($C_1$–$C_{16}$) alkyl, or ($C_1$–$C_{16}$) alkyl substituted with COOH, phenyl, or phenyl substituted with halo, hydroxy, amino, nitro, ($C_1$–$C_4$) alkoxy, or COOH;

$R^{14}$ is H or ($C_1$–$C_4$) alkyl;
and salts and complexes thereof.

More specifically, the invention provides a plant fungicide method which comprises applying a fungicidally effective amount of a compound of formula (I) to the locus of a plant pathogen.

The invention also provides a plant fungicide composition which comprises a compound of formula (I) in combination with a phytologically acceptable carrier.

Some of the compounds of formula (I) are known compounds. For example, U.S. Pat. No. 4,467,122 discloses a method of preparing 9,9-bis-(4-hydroxyphenyl)fluorene and discloses use of the compound in polyester resins. U.S. Pat. No. 4,707,534 describes use of various ortho-substituted 4-hydroxyphenylfluorenes in preparation of diglycidyl ethers that are useful in epoxy resin compositions.

It was not previously known that compounds of formula (I) have useful plant fungicide activity.

DETAILED DESCRIPTION OF THE INVENTION

Compounds of formula (I) wherein x is a single bond connecting the two adjacent carbon atoms are fluorene derivatives.

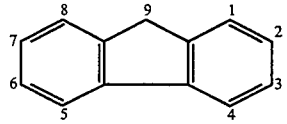

Compounds of formula (I) wherein X is $CH_2$ are 9,10-dihydroanthracene derivatives.

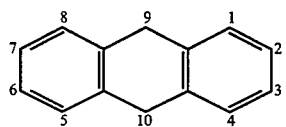

Compounds of formula (I) wherein X is O are xanthene derivatives.

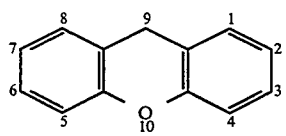

Compounds of formula (I) wherein X is S, SO, or $SO_2$, are thiaxanthene derivatives.

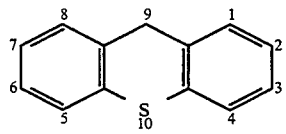

Compounds of formula (I) wherein X is NH are 9,10-dihydroacridine derivatives.

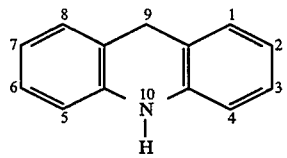

Preferred methods in accordance with the invention use compounds of formula (I) from the following classes:
(a) compounds of formula (I) wherein at least six of $R^1$, $R^2$, $R^3$, $R^4$, $R^5$, $R^6$, $R^7$, and $R^8$ are H;
(b) compounds of formula (I) wherein $R^1$, $R^2$, $R^3$, $R^4$, $R^5$, $R^6$, $R^7$, and $R^8$ are H;
(c) compounds of formula (I) wherein at least one of $R^{4'}$ and $R^{4''}$ is OH;
(d) compounds of formula (I) wherein $R^{4'}$ and $R^{4''}$ are OH;
(e) compounds of formula (I) wherein $R^{3'}$, $R^{5'}$, $R^{6'}$, $R^{3''}$, $R^{5''}$, and $R^{6''}$ are H and $R^{4'}$ and $R^{4''}$ are OH.

Throughout this document, all temperatures are given in degrees Celsius, and all percentages are weight percentages unless otherwise stated.

The term "halo" refers to P, Cl, Br, and I atoms.

The term "alkyl" refers to straight and branched hydrocarbon chains.

The terms "haloalkyl" and "haloalkoxy" refer to alkyl and alkoxy groups substituted with one or more halo atoms.

The term "substituted ($C_1$-$C_4$) alkyl" refers to an alkyl group subtituted with one or more groups selected from halo, halo ($C_1$-$C_3$) alkoxy, phenyl, amino, or amino substituted with one or two ($C_1$-$C_4$) alkyl groups or one ($C_1$-$C_4$) alkanoyl group.

The term "substituted ($C_2$-$C_4$) alkenyl" refers to an alkenyl group substituted with halo or halo ($C_1$-$C_3$) alkoxy;

The term "substituted benzyl" refers to a benzyl group in which the phenyl ring is substituted with up to three groups selected from halo, ($C_1$-$C_{10}$) alkyl, branched ($C_3$-$C_6$) alkyl, halo ($C_1$-$C_4$) alkyl, hydroxy ($C_1$-$C_4$) alkyl, ($C_1$-$C_4$) alkoxy, halo ($C_1$-$C_4$) alkoxy, phenoxy, substituted phenoxy, phenyl, substituted phenyl, $NO_2$, OH, CN, ($C_1$-$C_4$) alkanoyloxy, or benzyloxy.

The terms "substituted phenyl" and "substituted phenoxy", refer to such groups wherein the phenyl ring is substituted with up to three groups independently selected from halo, I, ($C_1$-$C_{10}$) alkyl, branched ($C_3$-$C_6$) alkyl, halo ($C_1$-$C_7$) alkyl, hydroxy ($C_1$-$C_7$) alkyl, ($C_1$-$C_7$) alkoxy, halo ($C_1$-$C_7$) alkoxy, phenoxy, substituted phenoxy, phenyl, substituted phenyl, $NO_2$, OH, CN, ($C_1$-$C_4$) alkanoyl, benzoyl, ($C_1$-$C_4$) alkanoyloxy, ($C_1$-$C_4$)alkoxycarbonyl, phenoxycarbonyl, or benzoyloxy.

Representative examples of groups of the formula

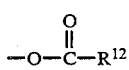

include formate, acetate, stearate, benzoate, phthalate, succinate, and glutarate.

A representative example of a group of the formula

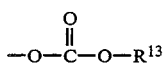

is methoxyformyloxy.

Various hydrates, salts and complexes of compounds of formula I can be made in the conventional way, and these derivatives are also useful in the method provided by this invention. Salts of compounds of formula (I) may be formed by replacing one or more of the phenolic hydrogen atoms with a cation, for example, $NH_4^+$, $^+N(CH_3)_4$, and $^+N(Bu)_4$, $K^+$, $Na^+$, $Ca^{++}$, $Li^+$, $Mg^{2+}$, $Fe^{2+}$, $Cu^{2+}$. It is believed that such salts may provide an advantage in preparation of soluble liquid formulations. Hydrates and amine complexes, in which the phenolic hydrogen atom is not completely displaced, but is shared with a molecule having an atom with an unshared pair of electrons have also been found to be useful. The compounds also form other complexes, for example with [$2+Cu(NH_3)_4Cl_2^{2-}$], that are useful in the claimed method.

SYNTHESIS OF COMPOUNDS

Compounds of formula (I) can be prepared using well known procedures and starting materials that are commercially available or are readily synthesized using standard procedures, for example the procedures illustrated in the following schemes and detailed examples.

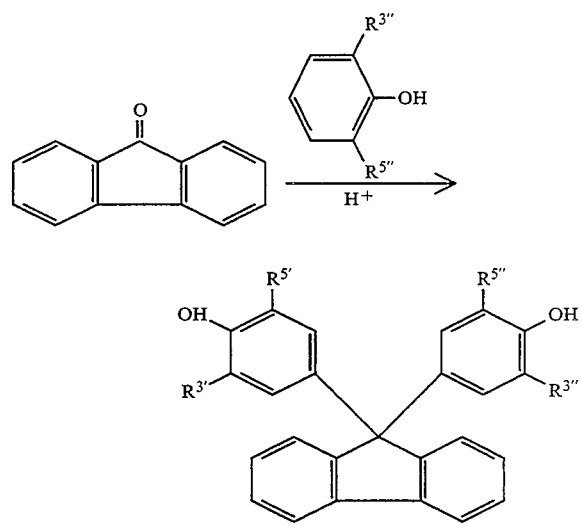

Scheme 1

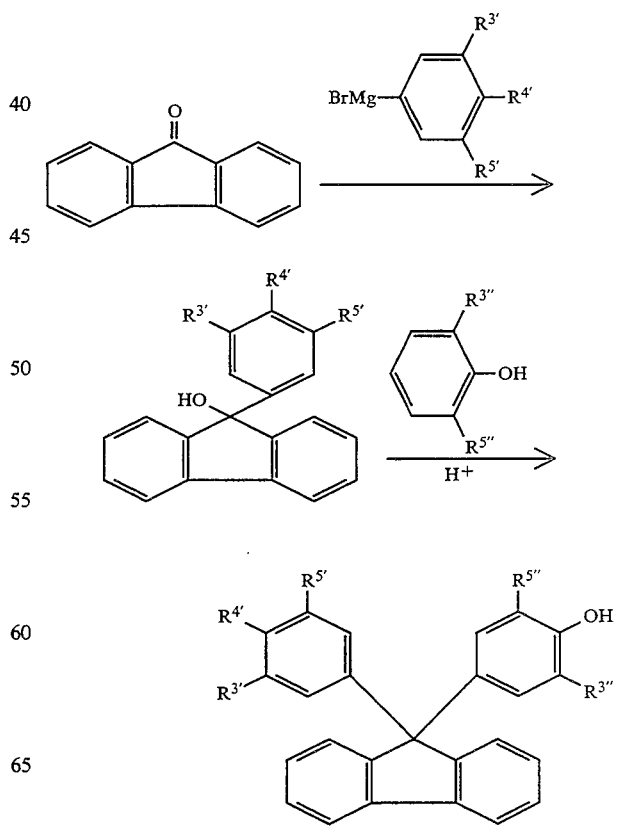

Scheme 2

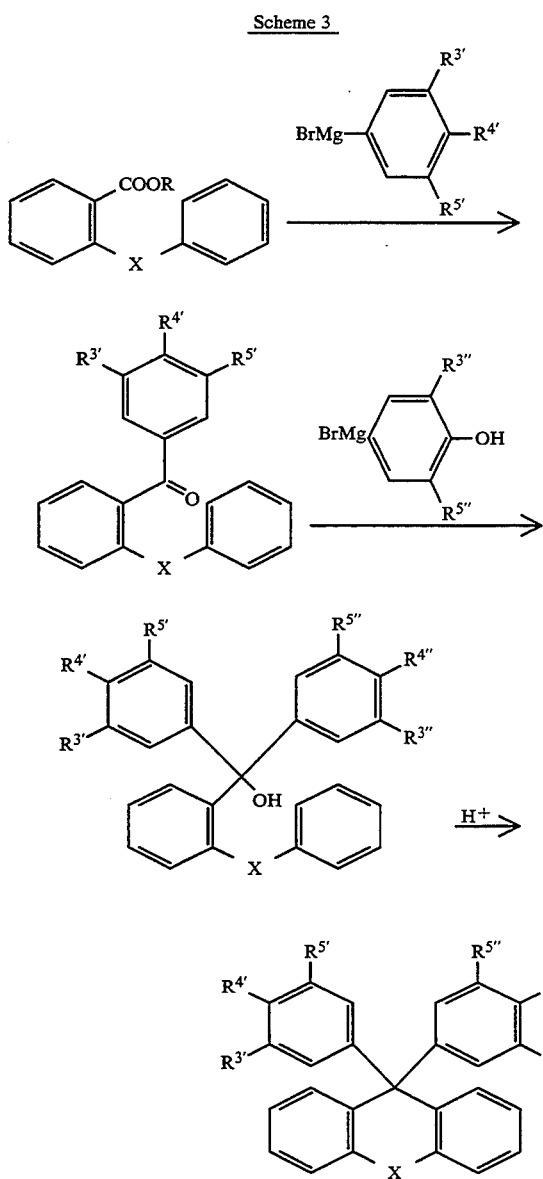

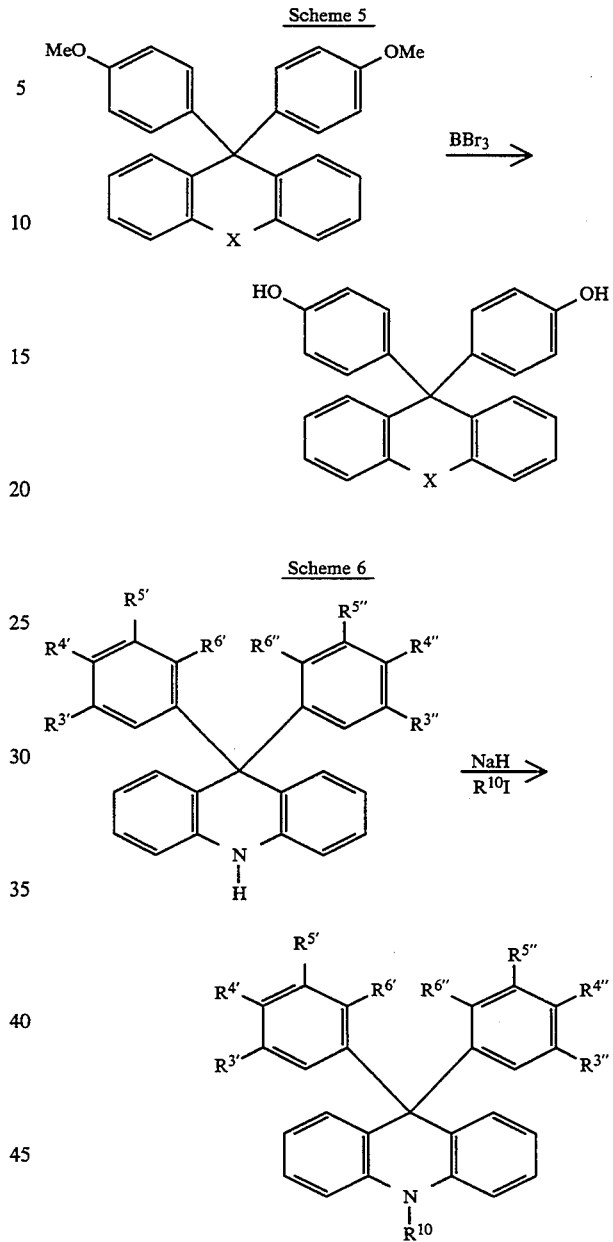

Example 1

9,9-bis-(4-hydroxyphenyl)fluorene (Compound 1)

9-Fluorenone (18.0 g, 99 mmol), phenol (37.6 g, 400 mmol) and 3-mercaptopropionic acid (0.8 g, 7 mmol) were heated to 60° C. under nitrogen. When all the solid had melted, dry hydrogen chloride gas was bubbled through the solution for 2 hours. The mixture was then heated at 80° C. for four hours. A solid formed, which was isolated by filtration. Excess phenol was distilled off under vacuum. The resulting solid was then recrystallized from toluene/hexane to give the title compound (26.0 g) as a solid. M.P. 215° C.

Example 2

Ethyl 9,9-bis-(4-hydroxyphenyl)fluorene-2-carboxylate (Compound 5)

Using the method of Example 1, 9,9'-bis-(4-hydroxyphenyl)fluorene-2-carboxylic acid was obtained from fluorenone 2-carboxylic acid (10.0 g) in 87% yield as a white solid (15.3 g). M.P. 281° C. This carboxylic acid was then refluxed for 6 hours under nitrogen in ethanol that had been pretreated with 5 mL of acetyl chloride. The excess solvent was then removed in vacuo and the residue was neutralized with sodium bicarbonate solution and extracted with ethyl acetate. The organic exracts were dried (MgSO$_4$), filtered, evaporated in vacuo, and recrystallized from ethyl acetate/hexane (9:1 (v/v)) to give the title compound as a cream colored solid (4.1 g). M.P. 280° C.

Example 3

9-(4-hydroxyphenyl)-9-(methyl-4-hydroxyphenyl)fluorene (Compound 14)

4-Bromoanisole (46.7 g) was added dropwise to a stirred mixture of magnesium (6.0 g) in dry THF (250 mL). When all the magnesium had dissolved, 9-fluorene (40.0 g) in THF (400 mL) was added dropwise. The mixture was then stirred at room temperature for 3 hours and quenched with saturated ammonium chloride solution. The excess solvent was evaporated in vacuo and the residue extracted with ethyl acetate. The organic layers were dried (MgSO$_4$), filtered, evaporated and recrystallized from hexane/ether to give 9-hydroxy-9-(4-methoxyphenyl)fluorene as a solid (48.2 g) M.P. 91°-93° C. This trityl alcohol (3.2 g) and o-cresol (1.8 g) were dissolved in acetic acid (25 mL) and concentrated H$_2$SO$_4$) (0.5 mL) was added dropwise. A deep red color developed rapidly and the reaction mixture decolorized after 30 seconds. After five minutes, the mixture was poured into water, neutralized with NaOH solution, and extracted with ethyl acetate. The organic layers were dried (MgSO$_4$), filtered, evaporated in vacuo to give 9-(4-methoxyphenyl)-9-(3-methyl-4-hydroxyphenyl)fluorene (4.0 g) as an oil, which was used in the next step without further purification. Ethanethiol (3.7 g) was added dropwise to a stirred suspension of sodium hydride (2.3 g, 60% in mineral oil) in dry DMF (20mL). After the hydrogen bubbling had ceased, the above-mentioned oil was added and the mixture refluxed for 2 hours under nitrogen. The excess solvent was evaporated in vacuo and the residue extracted with ethyl acetate. The organic layers were dried (MgSO$_4$), filtered, evaporated in vacuo and the residue recrystallized from chloroform-hexane to give the title compound (2.5 g) as a solid. M.P. 186°-188° C.

Example 4

9-(4-fluorophenyl)-9-(4-hydroxyphenyl)fluorene (Compound 30)

Using the same method as described in Example 3, 9-(4-fluorophenyl)-9-hydroxyfluorene was obtained from 9-fluorene and 4-fluorophenyl magnesium bromide as a solid. M.P. 106° C. Treatment of this intermediate with phenol in the presence of acetic acid and concentrated H$_2$SO$_4$ gave the titled compound as a solid. M.P. 149° C.

Example 5

9-(3-hydroxyphenyl)-9-(4-hydroxyphenyl)fluorene (Compound 29)

Using the same method as described in Example 3, 9-(3-methoxyphenyl)-9-hydroxyfluorene was obtained from 9-fluorene and 3-methoxyphenyl magnesium bromide as a solid. M.P. 87° C. Treatment of this intermediate with phenol in the presence of lo acetic acid and concentrated H$_2$SO$_4$ gave 9-(4-hydroxyphenyl)-9 (3-methoxyphenyl)fluorene as an oil. Demethylation gave the title compound as a solid M.P.221° C.

Example 6

9,9-bis-(4-hydroxyphenyl)-(9H, 10H)-dihydroanthracene (Compound 39)

Methyl 2-benzylbenzoate (10.0 g) was added dropwise to a stirred solution of 4-methoxyphenyl magnesium bromide, which was prepared in situ from magnesium (3.2 g) and 4-bromoanisole (24.9 g), in THF at room temperature. After 16 hours, the mixture was quenched with ammonium chloride solution and the solvent evaporated in vacuoo The residue was extracted with ethyl acetate, dried (MgSO$_4$), filtered, and evaporated in vacuo to give di-(4-methoxyphenyl)-(2-benzylphenyl)carbinol as an oil. This oil was dissolved in acetic acid (50 mL) and concentrated H$_2$SO$_4$ (2.0 mL) was added the resulting mixture was heated to 100° C. for one hour and then neutralized with NaOH solution. The mixture was extracted with ether and the organic extracts were combined, dried (MgSO$_4$), filtered, evaporated in vacuo and chromatographed on silica gel eluting with hexane/ethyl acetate (10/1) to give 9,9-bis(4-methoxyphenyl)-(9H, 10H)-dihydroanthracene (7.1 g) as a solid. M.P. 138°-140° C. Demethylation was performed using the sodium ethanethiolate/DMF procedure described in Example 3 to give the title product in 77% yield as a solid. M.P. 230°-232° C.

Example 7

9,9-bis-(4-hydroxyphenyl)-(9H)xanthene (Compound 40)

The title compound is obtained from methyl 2-phenoxybenzoate using the procedure described in Example 6. M.P. 220°-223° C.

Example 8

9,9-bis-(3-hydroxyphenyl)fluorene (Compound 31)

The title compound was obtained from 3-methoxyphenyl magnesium bromide and methyl 2-phenylbenzoate using the process of Example 6. M.P. 224°-228° C.

Example 9

9,9-bis-(4-hydroxyphenyl)-(9H)-acridine (Compound 43)

The title compound was obtained from methyl N-phenylanthranilate using the process of Example 6, except that demethylation in this example was performed with boron tribromide in dichloromethane at 0° C. for 16 hours. M.P. 247° C.

Example 10

N-Methyl 9,9-bis-(4-hydroxyphenyl)-(9H)-acridine (Compound 41)

The title compound was obtained from methyl N-methyl-N-phenylanthranilate using the process of Example 9. M.P. 261° C.

Example 11

9,9-bis-(4-hydroxyphenyl)-(9H, 10H)-10-hydroxy-10-methyl anthracene (Compound 50)

Compound 17 (15.5 g, 41 mmol) was dissolved in anhydrous THF (200 mL) under nitrogen and then cooled to 0° C. Methyllithium (30 mL, 205 mmol) was added dropwise and the reaction mixture was stirred at room temperature for four hours. The reaction was quenched by addition of ethanol (10 mL) followed by water (40 mL), then acidified to pH 1. The resulting mixture was allowed to stand for one hour, then the product was extracted into ethyl acetate (3×100 mL), dried (MgSO4), filtered and evaporated in vacuo to give a brown gum. This was dissolved in ethyl acetate and filtered through SiO2, evaporated in vacuo to give a light yellow solid. M.P. 234° C. Yield 71%.

Example 12

3,6-Dihydroxyspiro[fluorene-9-9'-xanthenel (Compound 62)

To a stirred mixture of fluorenone (27.0 g, 0.15 mol), 250 mL of acetic acid, and resorcinol (77.0 g, 0.70 mol) was added 3-mercaptopropionic acid (1 mL) followed by dropwise addition of 12 mL of methanesulfonic acid. The mixture was stirred at ambient temperature for 1 hr and then heated at 75° C. for 16 hr. The mixture was cooled, filtered, and the s filtrate was diluted with 100 mL of water. The colorless precipitate that formed was filtered, washed with water, and stirred with 200 mL of 10% NaOH solution for 1 hr. The solution was filtered, the filtrate was acidified with conc. HCL and the precipitate was filtered to afford the crude product. Recrystallization from DMF-water gave the title compound as a colorless powder (26.2 g, 49% yield) mp 262°–264° C.

Example 13

2,7-Dihydroxyspiro[fluorene-9-9'-xanthenel (Compound 63)

To a stirred solution of fluorenone (54.0 g, 0.3 mol), 750 mL of acetic acid, hydroquinone (132.0 g, 1.2 mol), and 3-mercaptopropionic acid (1 mL) was added dropwise 20 mL of methanesulfonic acid. The mixture was stirred and heated at 90° C. for 16 hr, another 10 mL of methanesulfonic acid was added, and heating and stirring was continued for 5 hr. After cooling to room temperature, the mixture was filtered and the filtrate was diluted with 300 mL of water. After stirring for 2 hr, the crude product that precipitated was filtered and recrystallized from DMF-water to afford the title compound as a colorless powder. (85.9 g, 79%) mp 261°–264° C.

Example 14

Compound 1 (6.74 g, 19.2 mmol) was dissolved in a solution of methanol (40 mL) and n-butylammonium hydroxide (25 mL, of 40% solution in MeOH). The resulting yellow solution was stirred at room temperature for four hours, then evaporated to give a colorless solid. This was washed in hot ethanol, filtered, and dried in vacuo to give a colorless solid. Elemental analysis indicated a complex with the ratio of 9-(4'-hydroxyphenyl)-9-(4''-hydroxyphenyl)fluorene and +N(n-Bu)4 being 2:1.

Example 15

Compound 1 (3.5 g, 10 mmol) and glutaric anhydride (1.5 g., 13 mmol) were dissolved in pyridine (50 mL) and the solution was stirred for three hours at room temperature, then evaporated to remove pyridine. The resulting syrup was partitoned between methylene chloride and 1M hydrochloric acid (20 mL) and water to convert the pyridinium salt into free acid. The extract was washed with water, then with saturated brine, and then dried with MgSO4 and evaporated to give the product as a foam.

The following table identifies compounds of formula (I) that were made using the synthetic procedures illustrated in the foregoing schemes and detailed examples. The procedures used to evaluate the biological activity of the compounds are described in the section following the table.

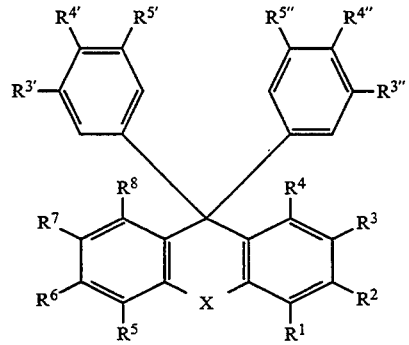

COMPOUND IDENTIFICATION

| cmpd | X | $R^{3'}$ | $R^{4'}$ | $R^{5'}$ | $R^{3''}$ | $R^{4''}$ | $R^{5''}$ | $R^1$ | $R^2$ | $R^3$ | $R^4$ | MP °C. | DOWN MDEW GRAPE 0 |
|---|---|---|---|---|---|---|---|---|---|---|---|---|---|
| 1 | — | H | OH | H | H | OH | H | H | H | H | H | 221–224 | +++ |
| 2 | — | Br | OH | H | Br | OH | Br | H | H | H | H | 220.1 | +++ |
| 3 | — | Br | OH | H | Br | OH | H | H | H | H | H | 145–147 | — |
| 4 | — | Cl | OH | H | Cl | OH | H | H | H | H | H | 168–170 | ++ |
| 5 | — | H | OH | H | H | OH | H | H | H | COOH | H | 281.4 | + |
| 6 | — | H | OH | H | H | OH | H | H | H | COOEt | H | 281 | +++ |
| 7 | — | H | OH | H | Br | OH | H | H | H | H | H | | + |
| 8 | — | H | OH | H | H | OH | H | H | H | COOMe | H | 178.6 | +++ |
| 9 | — | H | OH | H | H | OH | H | COOH | H | H | H | 267.5 | ++ |
| 10 | — | H | OH | H | H | OH | H | COOEt | H | H | H | 143.9 | +++ |
| 11 | — | H | OH | H | H | OH | H | COOMe | H | H | H | 240–241 | ++ |
| 12 | — | H | OH | H | H | OH | H | H | H | NH2 | H | 259–260 | +++ |
| 13 | — | H | OH | H | H | OH | H | H | H | F | H | 206–208 | +++ |
| 14 | — | Me | OH | H | H | OH | H | H | H | H | H | 186–188 | +++ |
| 15 | — | H | OH | H | F | OH | H | H | H | H | H | | ++ |

-continued

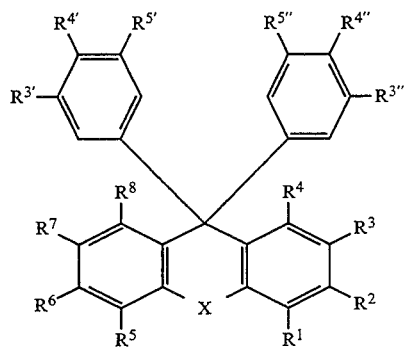

| cmpd | X | R3' | R4' | R5' | R3'' | R4'' | R5'' | R1 | R2 | R3 | R4 | MP °C. | DOWN MDEW GRAPE 0 |
|---|---|---|---|---|---|---|---|---|---|---|---|---|---|
| 16 | — | H | OH | H | H | OH | H | H | H | OH | H |  | +++ |
| 17 | — | H | OH | H | H | OH | H | H | NO₂ | H | H |  | +++ |
| 18 | — | H | OH | H | H | OH | H | H | NHCOOCH₃ | H | H | 230–232 | ++ |
| 19 | — | H | OH | H | H | OH | H | H | NHCH₃ | H | H | 116–118 | ++ |
| 20 | — | H | OH | H | H | OH | H | H | NHCHO | H | H | 274–278 | ++ |
| 21 | — | H | OH | H | H | OH | H | H | NO₂ | H | H | 238 | +++ |
| 22 | — | H | OH | H | H | OH | H | H | NCOOCH₃ | H | H |  | ++ |
| 23 | — | H | OH | H | H | OH | H | H | NCH₃ | H | H |  | ++ |
| 24 | — | H | OH | H | H | OH | H | H | NCHO | H | H |  | ++ |
| 25 | — | H | OH | H | H | OH | H | H | CH₂OH | H | H | 146 | +++ |
| 26 | — | H | OH | H | H | OH | H | CH₂OH | H | H | H | 253 | ++ |
| 27 | — | H | OH | H | H | OH | H | H | OMe | H | H |  | 0 |
| 28 | — | H | OH | H | H | OH | H | H | OH | H | H |  | 0 |
| 29 | — | H | OH | H | OH | H | H | H | H | H | H | 220.9 | +++ |
| 30 | — | H | OH | H | H | F | H | H | H | H | H | 149.2 | ++ |
| 31 | — | H | OH | H | H | H | H | H | H | H | H | 168–170 | +++ |
| 32 HCl | — | H | OH | H | H | NH₂ | H | H | H | H | H | 230 DEC 235 | + |
| 33 | — | H | OH | H | H | NH₂ | H | H | H | H | H | 235–237 | + |
| 34 | — | H | OH | H | H | OMe | H | H | H | H | H | 69–71 | + |
| 35 | — | OH | OH | H | H | OMe | H | H | H | H | H |  | + |
| 36 | — | H | OH | H | H | OOCMe | H | H | H | H | H | 90–92 | + |
| 37 | — | OH | H | H | OH | H | H | H | H | H | H | 224–228 | +++ |
| 38 | — | H | H | H | H | OH | H | OH | H | H | H |  | 0 |
| 39 | CH₂ | H | OH | H | H | OH | H | H | H | H | H | 230–232 | +++ |
| 40 | CO | H | OH | H | H | OH | H | H | H | H | H | >260 | ++ |
| 41 | NCH₃ | H | OH | H | H | OH | H | H | H | H | H | 260.9 | +++ |
| 42 | NEt | H | OH | H | H | OH | H | H | H | H | H | 200–202 | ++ |
| 43 | NH | H | OH | H | H | OH | H | H | H | H | H | 246.6 | +++ |
| 44 | Ni-Pr | H | OH | H | H | OH | H | H | H | H | H | 212–213 | +++ |
| 45 | NPr | H | OH | H | H | OH | H | H | H | H | H | 122–123 | ++ |
| 46 | O | H | OH | H | H | OH | H | H | H | H | H | 220–223 | +++ |
| 47 | S | H | OH | H | H | OH | H | H | H | H | H | 281–287 | +++ |
| 48 | O | H | OH | H | H | OMe | H | H | H | H | H | 152–154 | — |
| 49 | C=CH₂ | H | OH | H | H | OH | H | H | H | H | H | 258 | +++ |
| 50 | CCH₃OH | H | OH | H | H | OH | H | H | H | H | H | 234 | +++ |

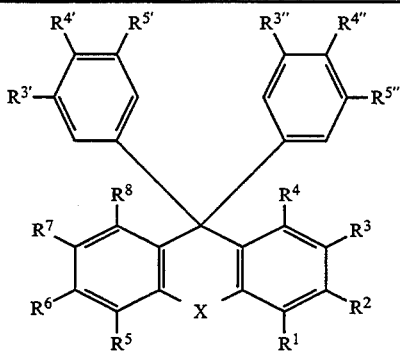

COMPOUND IDENTIFICATION

| cmpd | X | $R^{3'}$ | $R^{4'}$ | $R^{5'}$ | $R^{3''}$ | $R^{4''}$ | $R^{5''}$ | $R^1$ | $R^2$ | $R^3$ | $R^4$ | $R^5$ | $R^6$ | $R^7$ | $R^8$ | MP °C. | DOWN MDEW GRAPE |
|---|---|---|---|---|---|---|---|---|---|---|---|---|---|---|---|---|---|
| 51 | — | H | OH | H | H | OH | H | H | H | Br | H | H | H | Br | H | 280 | ++ |
| 52 | — | H | OH | H | H | OH | H | H | H | $NO_2$ | H | H | H | $NO_2$ | H | 330 | +++ |
| 53 | — | H | OH | H | H | OH | H | $NO_2$ | H | $NO_2$ | H | H | H | $NO_2$ | H |  | +++ |
| 54 | — | H | OH | H | H | OH | H | H | H | $C(CH_3)_2$ OH | H | H | H | H | H | 200 | +++ |
| 55 | — | H | OH | H | H | OH | H | H | H | Cl | H | H | H | Cl | H |  | +++ |
| 56 ($H_2O$) | — | OH | OH | H | H | OH | H | H | H | H | H | H | H | H | H |  | +++ |
| 57 | — | H | OH | H | H | OH | H | H | H | H | $CH_2OH$ | H | H | H | H | 258 | +++ |
| 58 | — | H | OH | H | H | OH | H | H | F | H | H | H | H | H | H |  |  |
| 59 | — | H | OH | H | H | OH | H | H | H | H | OH | H | H | H | H |  |  |
| 60 | — | H | OH | H | H | OH | H | $NO_2$ | H | $NO_2$ | H | $NO_2$ | H | $NO_2$ | H |  |  |
| 71 | — | H | OH | H | H | OH | H | H | H | H | F | H | H | H | H |  |  |

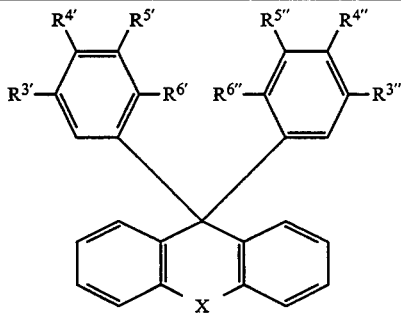

| cmpd | X | $R^{3'}$ | $R^{4'}$ | $R^{5'}$ | $R^{3''}$ | $R^{4''}$ | $R^{5''}$ | $R^{6'}$ | $R^{6''}$ | MP °C. | 400 ppm |
|---|---|---|---|---|---|---|---|---|---|---|---|
| 62 | — | H | OH | H | H | OH | H | —O— | |  | 0 |
| 63 | — | OH | H | H | OH | H | H | —O— | |  | 0 |
| 64 | — | H | OH | H | H | OH | H | OH | H | 224–228 | +++ |
| 65 | — | H | OH | H | H | H | H | H | OH | 200–201 | +++ |
| 66 | — | OH | H | H | H | H | H | H | OH | 230–231 | +++ |
| 67 | — | H | H | H | H | H | H | OH | OH | 230–231 | +++ |

Fungicide Activity

In accordance with the invention, compounds of formula (I) have been found to be effective plant fungicides. They are particularly effective against grape downy mildew. When employed in the treatment of plant fungal diseases, the compounds are applied to the plants in a disease inhibiting and phytologically acceptable amount. The term "disease inhibiting and phytologically acceptable amount," as used herein, refers to an amount of a compound of the invention which kills or inhibits the plant disease for which control is desired, but is not significantly toxic to the plant. This amount will generally be from about 1 to 5000 ppm, with 10 to 500 ppm being preferred. The exact concentration of compound required varies with the fungal disease to be controlled, the type formulation employed, the method of application, the particular plant species, climate conditions and the like. A suitable application rate is typically in the range from 0.25 to 5 kg/HA.

The following experiment was used to evaluate the efficacy of the compounds against *Plasmopara viticola* on grape vine The test compounds are formulated for application by dissolving 8 mg of the compound into 2 mL of acetone, using ultrasonication if necessary. A 0.5 mL aliquot of (8 mg/2 mL) sample is removed to a second container, leaving 6 mg/1.5 mL in the first container. 1.5 mL of acetone is added to the second container, the contents are mixed, and a 0.5 mL aliquot of (2 mg/2 mL) sample is removed to a third container, leaving 1.5 mg/1.5 mL in the second container. 1.5 mL of acetone is added to the third container, the contents are mixed, and a 0.5 mL aliquot of (0.5 mg/2 mL) sample is removed to a fourth container, leaving 0.375 mg/1.5 mL in the third container. 1.5 mL of acetone is added to the fourth container, the contents are mixed, and a 0.5 mL aliquot is removed and discarded, leaving 0.09375 mg/1.5 mL in the fourth container. To each of the four containers is added 13.5 mL of a 110 ppm solution of Triton X 100 in water. Final formulations contain 10% acetone, 100 ppm Triton X 100, and 400, 100, 25, and 6.25 ppm of test compound, respectively.

The formulated technical compounds were sprayed on all foliar surfaces of "Carignane" grape vine (*Vitis vinifera*) to past run-off.

Approximately 24 hours after the application of the test compounds, grape plants were inoculated with a suspension containing approximately 200,000 sporangia per mL on the lower leaf surface using a DeVilbis spray gun at 10 psi. The plants were then incubated at 21°±1° C., relative humdidity 95-100% for 6 to 7 days. The greenhouse fluorescent lights were on a 14/10 hour day/night cycle. The plants were exposed to approximately 8 hours of light immediately after inoculation. Untreated control plants and plants sprayed with a solvent surfactant blank were included in the test. After the incubation period, the disease symptoms were evaluated. Percent infection was scored from each plant and expressed as a percent of the solvent-surfactant control blank. The effectiveness of test compounds in controlling disease was rated using the following scale.

0 = not tested against specific organism
− = 0–19% control at 400 ppm
+ = 20–89% control at 400 ppm
++ = 90–100% control at 400 ppm
+++ = 90–100% control at 100 ppm Compositions The compounds of formula (I) are applied in the form of compositions which are important embodiments of the invention, and which comprise a compound of formula (I) and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be agglomerated to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates or synthetic precipitated silicas. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide adducts of alkyl phenols.

Emulsifiable concentrates of the compounds comprise a convenient concentration of a compound, such as from about 50 to about 500 grams per liter dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional non-ionic surfactants, such as those discussed above.

Aqueous suspensions comprise suspensions of water-insoluble compounds of this invention, dispersed in an aqueous vehicle at a concentration in the range from about 5% to about 50% by weight. Suspensions can be prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

The compounds of formula (I) can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

Adjuvants may be added, e.g. polyvinylacetate/polyvinyl alcohol copolymer, commonly described as a percentage hydrolysed polyvinylacetate. Typically the percentage hydrolysis is from 20 to 99.5%, with a molecular weight in the range of 2,000 to 500,000.

The following formulation is typical of compositions useful in the practice of the present invention.

Formulation A 8.5% w/w Soluble Liquid (SL)

78 g of compound 1 was dissolved with stirring and warming to 60° C. in a mixture of 448.5 g of 1M sodium hydroxide solution and 393.9 g of DOWANOL DPM (The Dow Chemical Company). The resulting clear solution could be diluted into deionized water with no precipitation over 30 minutes.

Formulation B

10% W/W wettable powder 100 g of compound 1 was mixed with 50 g of TENSIOFIX BC222 (OMNICHEM) and 850 g of AIRFLO HVA/R clay (WATTS, BLAKE & BEARNE) in a hamer mill. When the mixture was well agitated and contained no lumps it was transferred to an air jet mill and was milled until the median particle size was about 3 μm. This product was easily wetted when added to water and produced no flocculation or aggregation.

In utilizing the foregoing formulations, it has been found that disease control can be significantly improved if the material is tank mixed with a poly(vinyl alcohol). An 88% hydrolyzed poly(vinyl alcohol) having a molecular weight of 10,000–30,000 (Aldich Chemical Company, Inc. catalog #18,463-22) at a concentration of about 0.25% by weight has been found to give very good results.

We claim:

1. A plant fungicide method which comprises applying to the locus of a plant pathogen a fungicidally effective amount of a compound of formula (I)

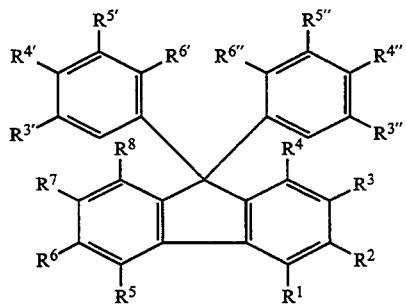

wherein:
$R^1$, $R^2$, $R^3$, $R^4$, $R^5$, $R^6$, $R^7$, and $R^8$ are independently H, halo, $NO_2$, ($C_1$-$C_4$) alkyl, or halo ($C_1$-$C_4$) alkyl;
$R^{3'}$, $R^{4'}$, $R^{5'}$, $R^{3''}$, $R^{4''}$, and $R^{5''}$ are independently H, halo, OH, or $CH_3$, provided that at least one is OH;
$R^{6'}$ and $R^{6''}$ are independently H or OH
and salts and complexes thereof.

2. A method of claim 1 wherein the compound of formula (I) is one wherein at least six of $R^1$, $R^2$, $R^3$, $R^4$, $R^5$, $R^6$, $R^7$, and $R^8$ are H.

3. A method of claim 1 wherein the compound of formula (I) is one wherein wherein $R^1$, $R^2$, $R^3$, $R^4$, $R^5$, $R^6$, $R^7$, and $R^8$ are H.

4. A method of claim 1 wherein the compound of formula (I) is one wherein at least one of $R^{4'}$ and $R^{4''}$ is OH.

5. A method of claim 1 wherein the compound of formula (I) is one wherein $R^{4'}$ and $R^{4''}$ are OH.

6. A method of claim 1 wherein the compound of formula (I) is one wherein $R^{3'}$, $R^{5'}$, $R^{6'}$, $R^{3''}$, $R^{5''}$ and $R^{6''}$ are H and $R^{4'}$ $R^{4''}$ are OH.

7. A method of claim 1 wherein the compound of formula (I) is 9,9-bis-(4-hydroxyphenyl)fluorene or a phytologically acceptable salt thereof.

8. A method of claim 1 wherein the compound is applied in a formulation containing a phytologically acceptable carrier and up to 90% by weight of a polyvinylacetate/polyvinyl alcohol compolymer having a molecular weight in the range from 2,000 to 50,000.

9. A plant fungicide composition which comprises a fungicidally effective amount of a compound of formula (I)

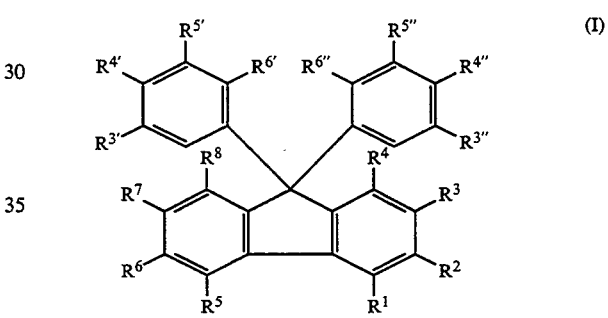

or a salt or a complex thereof, wherein:
$R^1$, $R^2$, $R^3$, $R^4$, $R^5$, $R^6$, $R^7$, and $R^8$ are independently H, halo, $NO_2$, ($C_1$-$C_4$) alkyl, or halo ($C_1$-$C_4$) alkyl;
$R^{3'}$, $R^{4'}$, $R^{5'}$, $R^{3''}$, $R^{4''}$, and $R^{5''}$ are independently H, halo, OH, or $CH_3$, provided that at least one is OH;
$R^{6'}$ and $R^{6''}$ are independently H or OH
in combination with a phytologically acceptable carrier, and including up to 90% by weight of a polyvinylacetate/polyvinyl alcohol compolymer having a molecular weight in the range from 2,000 to 50,000.

* * * * *